United States Patent [19]

Birck et al.

[11] Patent Number: 4,966,160

[45] Date of Patent: Oct. 30, 1990

[54] ACOUSTIC ADMITTANCE MEASURING APPARATUS WITH WIDE DYNAMIC RANGE AND LOGARITHMIC OUTPUT

[75] Inventors: Jonathan D. Birck, Portland; Valdis E. Garuts, Beaverton, both of Oreg.

[73] Assignee: Virtual Corporation, Portland, Oreg.

[21] Appl. No.: 914,462

[22] Filed: Oct. 2, 1986

Related U.S. Application Data

[63] Continuation of Ser. No. 788,746, Oct. 18, 1985, abandoned.

[51] Int. Cl.⁵ ............................................. A61B 5/12
[52] U.S. Cl. .................................... 128/746; 73/589; 73/585
[58] Field of Search .................. 128/746; 73/584–585, 73/589, 645–648; 381/101–102

[56] References Cited

U.S. PATENT DOCUMENTS

| | | | |
|---|---|---|---|
| 3,757,769 | 9/1973 | Arguimbau et al. | 128/746 |
| 4,009,707 | 3/1977 | Ward | 128/746 |
| 4,237,905 | 12/1980 | Keller et al. | 128/746 |
| 4,289,143 | 9/1981 | Canavesio | 128/746 |
| 4,429,702 | 2/1984 | Von Recklinghausen | 128/746 |

FOREIGN PATENT DOCUMENTS 0814336  3/1981  U.S.S.R. .............................. 128/746

Primary Examiner—Angela D. Sykes
Attorney, Agent, or Firm—Chernoff, Vilhauer, McClung & Stenzel

[57] ABSTRACT

An electrical circuit system for measuring the acoustic admittance of the ear cavity, for use in single and multiple tone tympanometry and acoustic reflex response testing, in which the probe tone applied to the ear cavity can be varied over a wide frequency range and a wide range of admittance variation can be measured. The signal output of the system, derived from the output signal of a microphone located in the ear cavity, is a DC voltage accurately proportional to the logarithm of the measured admittance of the ear cavity. An RMS to DC converter, an error integrator and an exponential element provide a closed control loop system for a variable gain amplifier so as to maintain the microphone output signal level constant regardless of admittance variations in the ear cavity. The level of the signal applied to the probe tone driver to accomplish this is a measure of the cavity admittance.

5 Claims, 4 Drawing Sheets

ACOUSTIC ADMITTANCE MEASURING APPARATUS WITH WIDE DYNAMIC RANGE AND LOGARITHMIC OUTPUT

This is a continuation of application Ser. No. 788,746, filed on Oct. 18, 1985, now abandoned.

BACKGROUND OF THE INVENTION

The present invention is directed to a circuit apparatus for measuring the acoustic admittance of the ear.

In the practice of tympanometry, measurements of the electrical impedance of the tympanic membrane of the inner ear (actually the admittance thereof, which is the reciprocal of the impedance) are made as ranges of air pressure or vacuum levels are applied thereto in the presence of tone signals of single, or more recently differing, frequency. The positive and negative pressure levels are applied to the eardrum via a probe inserted into the ear which also serves to apply the acoustic tone levels and act as a microphone to measure the admittance of the tympanic membrane in response to the tone stimulus as pressure changes are made. A number of tympanometry testing instruments are commercially available to the practitioner; including those made by Amplaid Spa, of Milan, Italy, Grason-Stadler, of Littleton, Mass., and Madsen Electronics, of Oakville, Ontario and Buffalo, N.Y. However, at present, the existing tympanometric instrumentation in the market allows only a few frequency tones to be applied to the eardrum, typically the standard frequency tones of 226 and 678Hz. To expand the range of diagnostic evaluation in this field it is desirable to perform multiple frequency tympanometric measurements and thus to be able to apply to the ear cavity via a probe selected tones at various frequencies over the mid-sonic range. During tympanometry, it is desirable to have a fast response to changes in the ear cavity's admittance in order to reduce the total measurement time and to track the changes in admittance. On the other hand, in another type of test, when a stimulus tone signal is present together with a standard probe tone level signal in measuring the acoustic reflex response of the ear, it is desirable that the bandpass filter have a narrow bandwidth in order to better reject large amplitude stimulus signal which may be up to 40 dB above the probe tone level.

BRIEF SUMMARY OF THE INVENTION

The system of the present invention enables, in an acoustic admittance measuring system, selected probe tones over the frequency range of about 150 to about 2.5 KHz to be applied as a stimulus to the ear cavity via an acoustic probe, and then to measure the response of the tympanic membrane, as represented by its electrical admittance and changes therein. (Limitations in the mechanics of the probe design may reduce the effective upper frequency limit for measuring response characteristics to about 1 KHz.) The herein disclosed circuitry provides a simple and inexpensive means for accurately measuring a wide range of admittance variation (in excess of 40 dB) in response to probe tones varied within the aforedescribed range.

The innovative advantages and features of the acoustic admittance measuring system of the present invention include:

The probe tone level within the ear cavity is maintained constant regardless of ear size and/or the static pressure level.

The system is insensitive both to interference from noise and to the presence of much larger signals at frequencies different from the probe tone, such as stimulus tones.

The system's dynamic response to rapidly varying admittance is independent of the mean admittance level.

The signal output of the system is a DC voltage accurately proportional to the logarithm of the admittance (in decibels).

A noise-free, constant amplitude version of the probe tone within the ear cavity is provided by the system for use in phase determination, if desired.

An electronically-tunable bandpass filter is used to reject interfering signals and to permit rapid electronic control of the probe tone frequency.

An integrating error amplifier is provided to maintain the cavity probe tone level at a constant value.

An exponential element is employed, inside the level control loop for the circuit, to provide a DC output proportional to the cavity's admittance while maintaining constant loop gain and loop dynamics regardless of cavity admittance.

The foregoing and other objectives, features, and advantages of the invention will be more readily understood upon consideration of the following detailed description of the invention, taken in conjunction with the accompanying drawing.

DETAILED DESCRIPTION OF THE INVENTION

Figure 1:
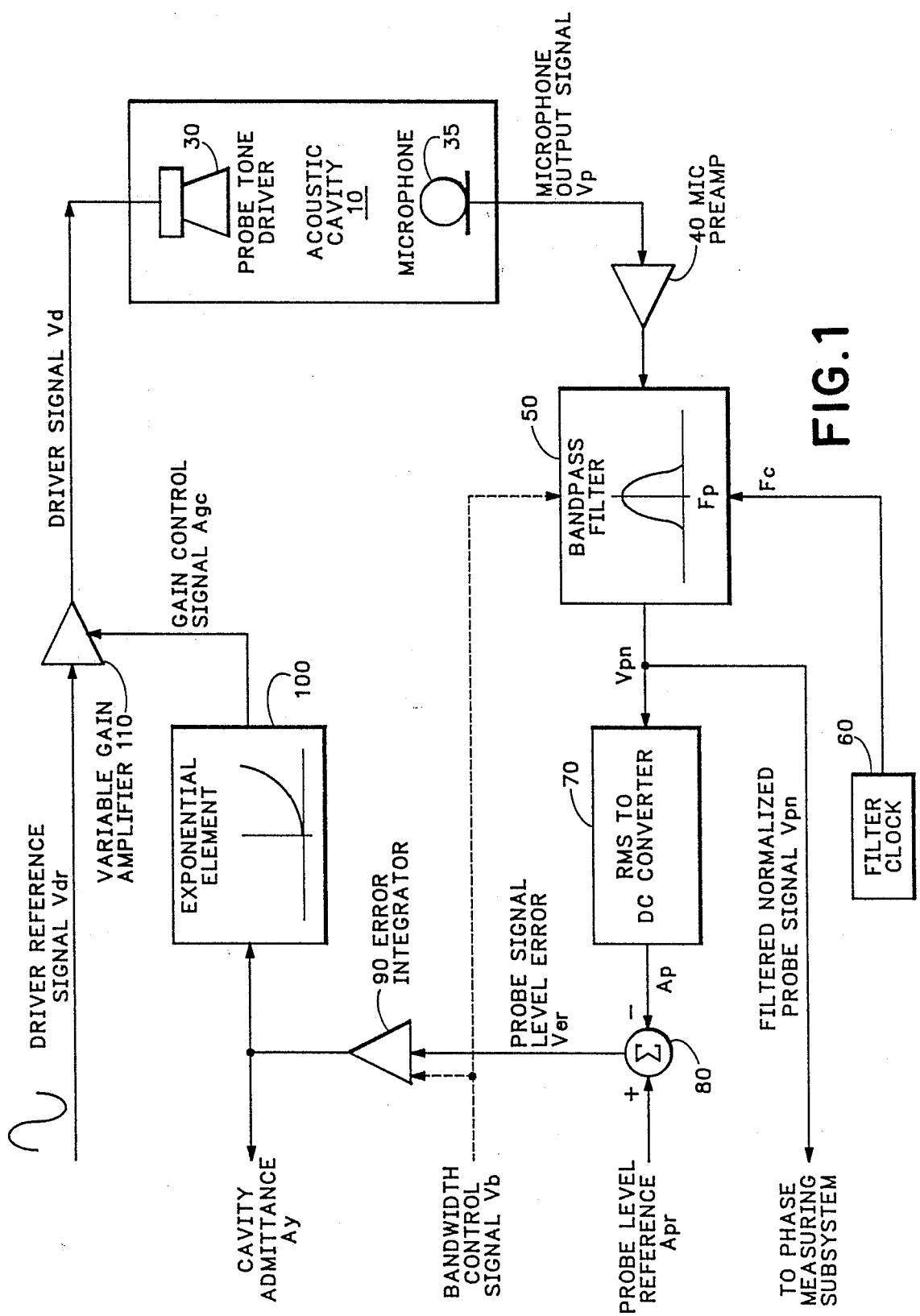
FIG. 1 is a block diagram of an apparatus of the present invention for measuring acoustic admittance in multiple frequency tympanometry and acoustic reflex response testing and analysis.

The functional components of the system shown in the block diagram of FIG. 1 are arranged in a closed control loop which automatically adjusts the output of the Probe Tone Driver 30 within the Acoustic Cavity 10 so that the Microphone Output Signal Vp from the Microphone 35 is constant regardless of cavity admittance variations. The level of the signal Vd applied to the driver to accomplish this is a measure of the cavity's admittance.

The Microphone Output Signal Vp is amplified to a suitable level by the Microphone Preamplifier 40, and applied to the Bandpass Filter 50. The filter's passband is centered about the probe tone frequency Fp. The filter is built from a switched capacitor filter element, such as the MF10 marketed commercially by National Semiconductor and other suppliers, which allows the center frequency to be controlled over a wide range by the frequency Fc of the Filter Clock 60. The Bandpass Filter 50 has a relatively narrow bandwidth (approximately 10% to 25% of the center frequency Fp), and sharply increasing attenuation outside the passband, which prevents interfering signals from being passed to the rest of the system.

The filtered, normalized probe signal Vpn is passed to the RMS to DC Converter 70 which outputs a DC voltage Ap proportional to the RMS value of the probe tone. Since in operation the signal level at the converter input is constant, the accuracy of the converter is not important, only its stability. The filtered probe tone signal Vpn is also at a suitable level for use as an output in a phase measuring subsystem (not shown).

The RMS to DC Converter output Ap is subtracted (by current summing at summer 80) from the Probe Level Reference signal Apr. The difference is the Probe Signal Level Error Ver, and it is applied to the Error Integrator 90 whose output is the time integral of the error. The integrated error signal Ay is input to an Exponential Element 100 whose output (a current level) Agc is accurately proportional to the exponential function ($e^x$) of its input.

The probe tone Driver Reference Signal Vdr is a constant amplitude sinewave at the probe frequency Fp. It is applied to the signal input of a Variable Gain Amplifier 110. The amplifier's gain, and therefore also its output Yd, are proportional to the Gain Control Signal Agc. Assuming that the gain of the Probe Tone Driver 30 is also fixed, the Gain Control Signal and the Probe Driver's Tone acoustic output are proportional.

The control loop is closed by the sound level at the Microphone 35, which determines the Microphone Output Signal Vp. The feedback around the loop is negative, so that an increase (or decrease) in microphone output causes a decrease (or increase) in driver output.

The use of an integrating error amplifier 90 means that, on average, the RMS to DC Converter output Ap must exactly equal the Probe Level Reference Apr. Otherwise, the Error Integrator's output continues to change and, via the Exponential Element and variable Gain Amplifier, changes the Driver Signal Vd until equality is established. Therefore, the probe tone sound level at the Microphone is also accurately constant since it is related to the RMS to DC Converter's output by the fixed gain of the preamplifier/filter/converter chain. Given a constant cavity sound level, the amplitude Vd of the Driver Signal required to accomplish this level is proportional to the cavity's acoustic admittance. The input signal Ay to the Exponential Element 100 is proportional to the logarithm of its output Agc. Since this output is proportional to the Driver Signal Vd, the input (which is also the Error Integrator's output) is proportional to the logarithm of the Acoustic Cavity's admittance.

The aforesaid logarithmic relationship provided as an output signal Ag by the operation of the Exponential Element 100 permits the admittance to vary widely while the output per percent admittance change remains constant. A relatively low resolution and inexpensive analog-to-digital converter (not shown) can then be provided to convert this signal output while still maintaining constant percentage resolution. The accuracy and acceptable acoustic admittance range of this portion of the system depends on the accuracy of the Exponential Element. This is preferably implemented by using the exponential relationship existing between the collector current and base-to-emitter voltage of a silicon bipolar transistor which, in modern transistors, is very accurate over several decades of current levels.

An additional result of using the Exponential Element inside the feedback loop is that the incremental loop gain (expressed, for example, as the percent change in driver output per percent change in microphone input) is constant, regardless of the Driver Signal level Vd. Therefore, the static and dynamic response of the system to slow and fast cavity admittance changes is independent of the cavity admittance—a very desirable characteristic.

In the system of FIG. 1 there is shown therein a means for accomplishing a rapid change in the cavity's admittance, and thus the response speed of the system, by electronically increasing (or, alternatively, decreasing) the bandwidth of the Bandpass Filter 50, to which the signal Vp from the Microphone 35 is inputted, in response to the Control Signal Vb. The bandwidth of the Error Integrator 90 is also increased (or decreased) in the same proportion as the Bandpass Filter's bandwidth in order to maintain a clean dynamic system step response, with fast settling to the final value and minimum overshoot and ringing.

Figure 2A:
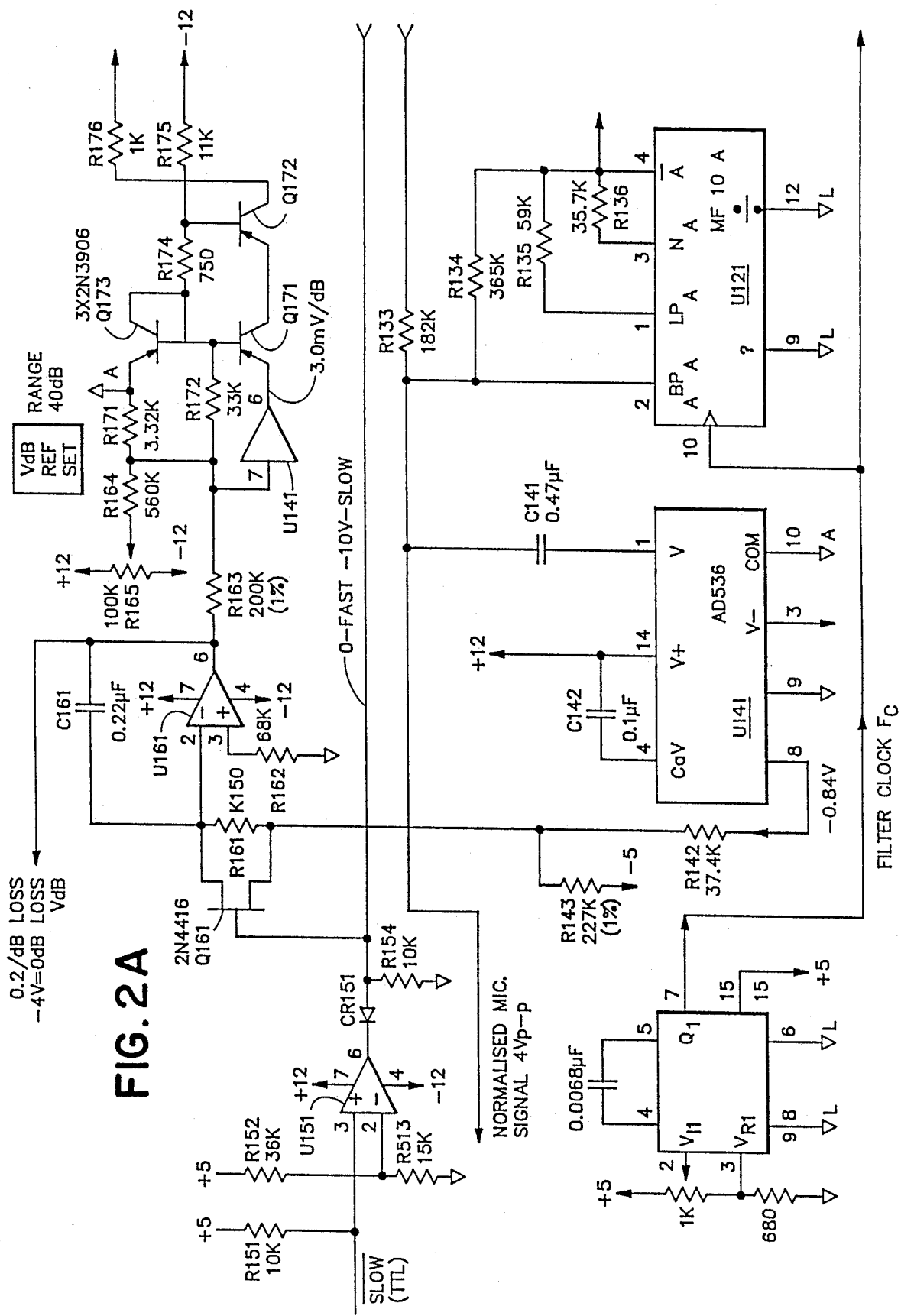
FIG. 2A is a first portion of an electrical schematic diagram illustrating an exemplary circuit which embodies the acoustic admittance measuring apparatus of the present invention.
Figure 2B:
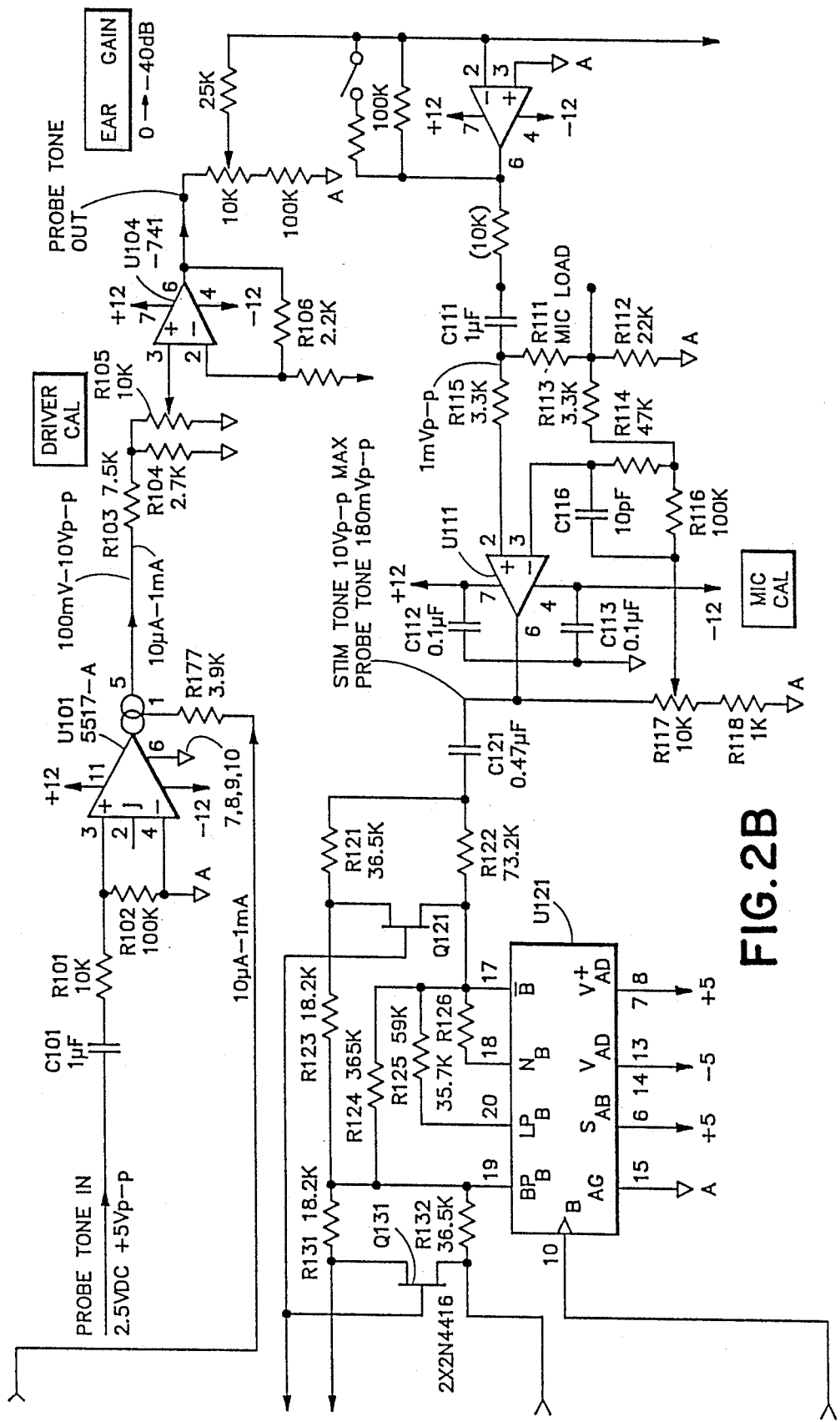
FIG. 2B is a second portion of the electrical schematic diagram of the present invention and is a continuation of the schematic diagram of FIG. 2A.
Figure 2C:
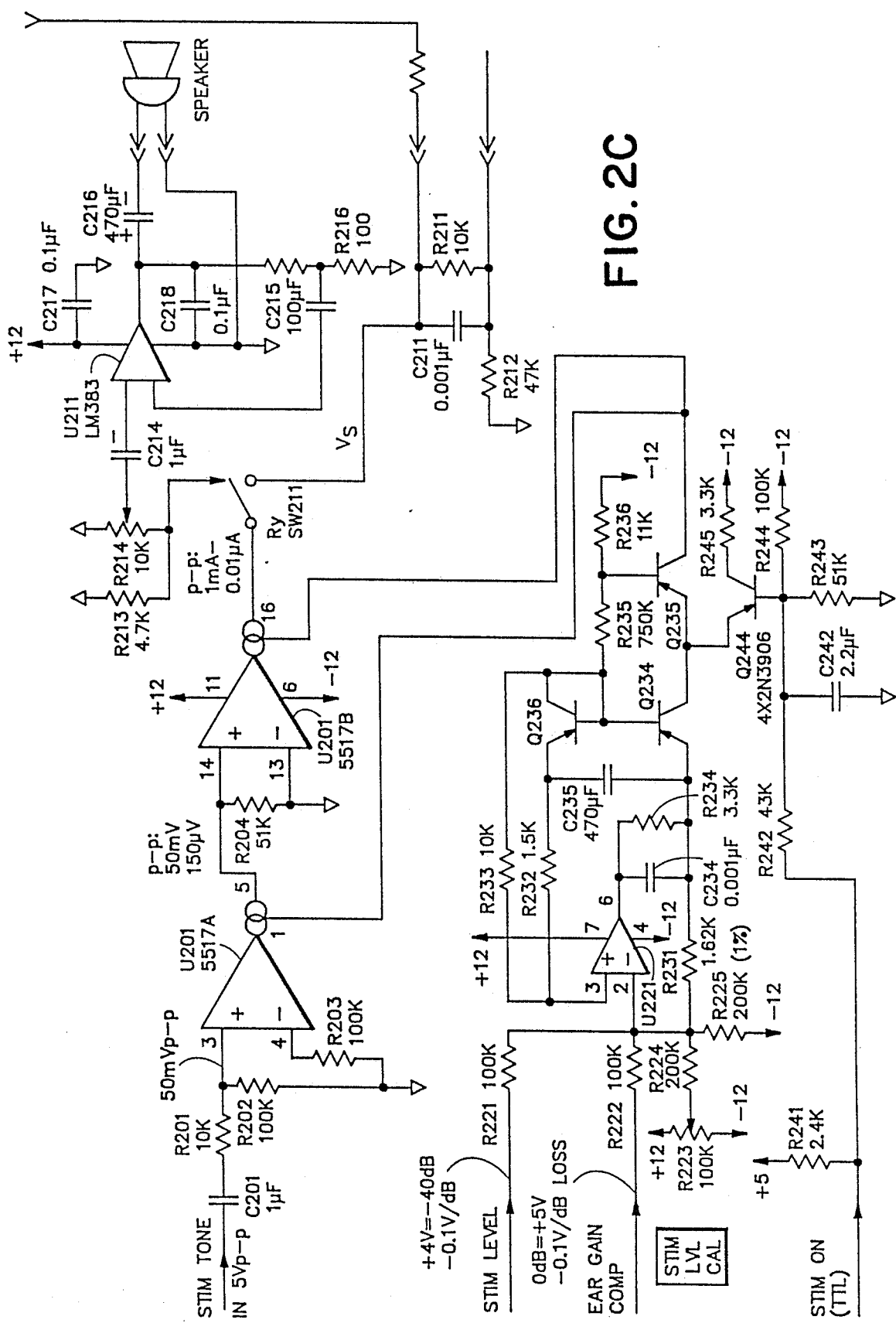
FIG. 2C is a third portion of the electrical schematic diagram of the present invention and is a continuation of the schematic diagram of FIG. 2B.

An exemplary circuit for implementing the above-described acoustic admittance measuring system is shown in the schematic diagram of FIG. 2. The Variable Gain Amplifier 110 is U101 and associated components; the Microphone Preamp 40 is U111 and associated components; the Bandpass Filter 50 is U121 and associated components; and the RMS to DC Converter 70 is U141 and associated components. The Probe Level Reference Apr is the current through R143, and the RMS to DC Converter output Ap is the current through R142 The Error Integrator 90 is U161 and associated components; and the Exponential Element 100 is Q171, and associated components, which is driven by a low impedance buffer forming a part of U141.

Bandpass Filter 50 is built from an MF10 switched capacitor filter element U121. In narrow bandwidth operation FET (field effect transistor) switches Q121 and Q131 are set to OFF (with the gates at approximately −11V) and the bandwidth is determined by R124 and R134. To increase the bandwidth, without changing the center frequency of the filter these resistors must be reduced proportionately. However, the gain at center frequency Fp depends on the resistor ratios R124/R122 and R134/R132. In the exemplary embodiment of the invention shown, the required switching to wide bandwidth is accomplished by turning ON FET switches Q121 and Q131 through the medium of switching the gates to zero volts. This step connects R123, R133, respectively, in parallel with R124, R134, respectively, to increase bandwidth, and also connects R121, R131, respectively, in parallel with R122, R132, respectively, to maintain constant the gain at center frequency of the bandpass Filter.

The Error Integrator 90 is built from element U161 and its gain × bandwidth product is determined by 1/(C161×error signal source resistance). For a narrow bandwidth, FET switch Q161 is set to OFF (i.e., gate at approximately ×11V),a nd the source resistance is then R161 in series with the combination of R142 in parallel with R143. However, for wide bandwidth operation, Q161 is turned to ON (gate to zero volts) with the result that the signal source resistance is now merely R142 in parallel with R143 (plus the negligibly small resistance of the FET when in the ON condition), and the bandwidth of the Error Integrator is increased as required.

Amplifier U151 and associated components are used as a level translator for converting the Bandwidth Control Signal Vb to the −11V or zero volts signal as required to control the FET switches Q121, Q131 and Q161 in the Bandpass Filter and error Integrator, respectively.

The terms and expressions which have been employed int eh foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An electrical circuit apparatus for measuring the acoustic admittance of the ear cavity in response to probe tone frequency signals applied for tympanometry and acoustic reflex testing, said apparatus comprising:
   (a) probe tone driver means for applying a probe tone to an ear cavity;
   (b) microphone means for providing an output signal responsive to the admittance of said cavity;
   (c) bandpass filter means coupled to receive said microphone output signal and having a band pass centered about the frequency of said probe tone;
   (d) converter means coupled to the output of said filter means for providing as an output a filtered DC representation of said microphone output signal;
   (e) summer means for algebraically combining the DC output of said converter means with a reference signal representing said probe tone to provide an error signal; and
   (f) exponential circuit element means responsive to said error signal for deriving a logarithmic signal to control said probe tone driver means.

2. The electrical circuit apparatus of claim 1 wherein said probe tone driver means includes a variable gain amplifier controlled by the output of said exponential circuit element means.

3. The electrical apparatus of claim 1 wherein said bandpass filter means has an effective bandwidth selectable between a narrow and a broad pass range.

4. In an electrical circuit apparatus for measuring the acoustic admittance of the ear cavity in response to probe tone frequency signals, comprising a variable gain amplifier for generating an input signal for a probe tone driver, sensing and signal processing means for providing an output signal which is representative of the admittance of said ear cavity, the improvement comprising:
   (a) exponential circuit element means responsive to said output signal for controlling said variable gain amplifier so that said input signal matches a reference input signal representative of a predetermined acoustic intensity level provided by said probe tone driver.

5. The electrical circuit apparatus of claim 4 wherein said signal processing means includes a variable bandpass filter whose pass band is selectable between a narrow pass range and a broad pass range.

* * * * *